United States Patent [19]

Spevak et al.

[11] Patent Number: 4,820,263
[45] Date of Patent: Apr. 11, 1989

[54] APPARATUS AND METHOD FOR IONTOPHORETIC DRUG DELIVERY

[75] Inventors: Richard Spevak, Minneapolis; Gary A. Lattin, Forest Lake; Allan H. Jevne, Anoka, all of Minn.

[73] Assignee: Medtronic, Inc., Minneapolis, Minn.

[21] Appl. No.: 105,929

[22] Filed: Nov. 7, 1987

Related U.S. Application Data

[62] Division of Ser. No. 241,150, Mar. 6, 1981, abandoned.

[51] Int. Cl.$^4$ .............................................. A61N 1/30
[52] U.S. Cl. .................................... 604/20; 128/798; 128/802
[58] Field of Search ................. 604/20; 128/639–641, 128/798, 802, 803

[56] References Cited

U.S. PATENT DOCUMENTS

| | | | |
|---|---|---|---|
| 2,784,715 | 3/1957 | Kestler | 128/172.1 |
| 4,142,521 | 3/1979 | Konikoff | 128/82.1 |
| 4,325,367 | 4/1982 | Tepper | 128/803 X |
| 4,383,529 | 5/1983 | Webster | 128/802 X |
| 4,398,545 | 8/1983 | Wilson | 128/798 |
| 4,416,274 | 11/1983 | Jacobsen et al. | 128/803 X |
| 4,633,879 | 1/1987 | Ong | 128/641 |

FOREIGN PATENT DOCUMENTS

| | | | |
|---|---|---|---|
| 1965195 | 7/1971 | Fed. Rep. of Germany | 128/640 |
| 410009 | 5/1934 | United Kingdom . | |
| 2045088 | 10/1980 | United Kingdom | 128/640 |

Primary Examiner—Lee S. Cohen
Attorney, Agent, or Firm—Reed A. Duthler; Joseph F. Breimayer; John L. Rooney

[57] ABSTRACT

An ionic substance is mixed with a polar, non-ionic adhesive to form an electrode for use in the iontophoretic introduction of the ionic substance into a body. The electrode may be formed as a sheet of the mixture of a size and shape suitable for attachment to the electrode plate of an iontophoretic current generator. The mixture may be incorporated in an electrode as a means for holding the ionic substance, a means for attaching the electrode to the body, a means for attaching the iontophoretic current generator to the body, or a means for conducting the ionic current into the body. The electrode may also be employed in combination with an electrical stimulator to provide for simultaneous electrical stimulation and iontophoretic drug administration to the body.

8 Claims, 1 Drawing Sheet

APPARATUS AND METHOD FOR IONTOPHORETIC DRUG DELIVERY

This is a divisional of application Ser. No. 241,150, filed on Mar. 6, 1981, now abandoned.

BACKGROUND OF THE INVENTION

1. Field of the Invention

This invention in general relates to an electrode, and is particularly applicable to the field of the iontophoretic introduction of an ionic substance into a body, where it may be used in the manufacture of simple and reliable electrodes incorporating an improved means of storing the ionized substance within the electrode, an improved means for iontophoretic conduction of substances into the body, and improved means for attaching the electrode to the body.

2. Description of the Prior Art

Iontophoresis is a method for introducing ionic substances into a body. The method utilizes direct electrical current to drive the ionized substances, such as chemicals or drugs, through the intact skin or other body surface. This has proven to be very useful in numerous medical applications. U.S. Pat. Noss. 3,991,755 issued to Jack A. Vernon, et al and 4,141,359 issued to Stephen C. Jacobsen, et al disclose examples of iontophoretic devices and some applications of the devices. The iontophoresis process has been found to be useful in the administration of lidocaine hydrochloride, hydrocortisone derivatives, acetic acid, fluoride, penicillin, dexamethasone sodium phosphate and many other drugs. Perhaps the widest use of iontophoresis is that of diagnosing cystic fibrosis by using pilocarpine nitrate iontophoresis. The pilocarpine nitrate stimulates sweat production; the sweat is collected and analyzed for its chloride or sodium content to detect the presence of the disease.

In iontophoretic devices two electrodes are used. One electrode, called the active electrode, is the electrode at which the ionic substance is driven into the body. The other electrode, called the indifferent or ground electrode, serves to close the electrical circuit through the body. It will be appreciated by those skilled in the art that the active electrode must hold, contain, or otherwise have available to it a source of the ionic substance. Thus, in the prior art the active electrode is generally relatively complex compared to the indifferent electrode.

U.S. Pat. No. 3,991,755 discloses several examples of active electrodes. In one example the electrode comprises a stainless steel wire housed in a plastic sheath which is shaped to safely fit within the ear canal together with a liquid solution containing the ionized substance, which liquid is poured into the ear canal so that it contacts the inner ear and the wire through an opening in the sheath. In another example, the electrode wire housed in a plastic sheath having an opening is placed in a wad of absorbent material which holds the liquid containing the ionic substance.

U.S. Pat. No. 4,141,359 also discloses several embodiments of an active electrode. All of the embodiments include a receptacle for holding either a conducting gel in which the ionic substance is dissolved, or for holding a sponge which is saturated with the conductive gel in which the ionic substance is dissolved. The conducting gel/ionic drug solution communicates with the body tissue through a hole in the receptacle. The receptacle is held in contact with the skin by an adhesive pad surrounding the receptacle or a strap attached to the pad. In other embodiments of the prior art the hole in the receptacle is covered with a membrane and the ionic substance is driven through the membrane by the electric current.

An active electrode formed by a gauze pad soaked in the solution containing the ionic substance superimposed by several layers of paper towels moistened with tap water and a section of block tin or aluminum foil placed over the moistened towel with the tin or foil connected to the iontophoretic current generator by means of a wire and alligator clip is disclosed in *Acetic Acid Iontophoresis for Calcium Deposits*, by Joseph Kahn in *Physical Therapy*, Vol. 57, No. 6, June, 1977 (pp. 658–659).

The active electrodes of the prior art have a number of disadvantages. Those in which the ionic substance is held in solution in a liquid are relatively messy. Of these, those in which the liquid is not contained in an absorbent material can be used only in situations where body cavities form a natural container for the liquid, or it is necessary to employ a cup or other container to hold the liquid about the body surface through which the ionic substance can be driven. The electrodes employing the conductive gel in which the ionic substance is dissolved are somewhat less messy, but still leave a residue of gel after use. The electrodes employing the membrane alleviate most of the above problem but create additional complexities in the construction and handling of the electrode, relating both to the membrane itself and the separate means for insertion of the ionic substance that is required if a membrane is used. In all of these electrodes, a separate strap or adhesive pad is necessary to hold the electrode in place, or alternatively the patient must remain still during the use of the ionotophoretic device so that the electrode will remain in place. Even with the use of a strap or adhesive pad the portion of the electrode containing the ionic substance is still subject to some movement due to the flexibility in such materials, and the flexibility of body tissue. Moreover, in all of these devices some of the liquid or gel may move away from the main body of the liquid gel, as for example by dripping out of the absorbent material or sliding under the edge of the adhesive pad. When this occurs, electrical contact may or may not be lost and the ionic substance in the dislocated portion of the material may or may not be driven into the body. The aforementioned disadvantages all result in an inability to precisely control the area over which the ionic substance is administered, which control is often necessary for drugs and other chemical agents for which the process is used. In addition to the complexities involved in applying the electrodes mentioned above, all of the active electrodes of the prior art require complex procedures for handling the material containing the ionic substance prior to and, in some electrodes, during the iontophoretic process. A simpler electrode would permit the iontophoretic process to be much more widely applied, not only in applications now known to be practiced, but also in many new applications that previously were not practical. For example, although electrical stimulation of body tissue for pain suppression and muscular therapy have been known for some time, (see, for example, U.S. Pat. No. 4,019,518) these treatments have not, up to now, been used in combination with iontophoresis, except on a limited clinical basis, since up to now iontophoretic electrodes have been too messy and complex for use by the average patient.

SUMMARY OF THE INVENTION

The invention provides an electrode for use in the iontophoretic introduction of an ionic substance into a body. The electrode consists essentially of an element composed of an adhesive material mixed with the ionic substance and includes a means for electrically coupling the element to an electrical device. Preferably the adhesive material is a non-ionic, polar material. Other substances may be included in the element so long as they do not materially and adversely affect the iontophoretic process and the adhesive quality of the mixture. The invention can take a wide variety of embodiments. In one embodiment the electrode comprises a sheet of the composition in any suitable size and shape. In one aspect of this embodiment the sheet may be applied to the body, and it may be connected to an iontophoretic generator by a wire. It is noted that in this aspect of the invention, the composition serves both as a container for the ionic substance, as the means for holding the electrode to the body, and the means for conducting the ionic substance into the body. In another aspect of this embodiment the sheet of material is of a size and shape suitable for application to the electrode plate of an iontophoretic current generator. If the electrical device is of the type in which the electrode plate is attached directly to the device, then it is seen that the composition may serve as the container for the ionic substance, the means for attaching the electrode to the body, the means for electrically coupling the element to the electrical device, the means for conducting the ionic substance into the body, and also as a means for attaching the electrical device to the body.

When the invention is understood, it will be appreciated that numerous advantages arise from the combination of the ionic substance with the adhesive in the electrode. It is evident that electrodes for iontophoretic devices can be made much simpler since the electrode conductive element may serve as its own receptacle. Thus receptacle structures such as a cup, absorbent swab, membranes, etc. of the prior art may be eliminated. Further, the electrode conductive element may also serve as a means for attaching the electrode to the body, and thus the straps, adhesive attachments pads, etc. of the prior art may be simplified or eliminated in some embodiments. It should be appreciated that the invention also provides for more precise delivery of dosages of the ionic substance, since the electrode composition tends to cling together and portions of it cannot easily become separated. Moreover, the entire active surface of the electrode is held firmly to the body, even under the condition of considerable movement of the body, which again serves to facilitate precise delivery and also serves to facilitate uniform dosage control over the body portion to which the electrode is applied.

It is noted that it is not necessary for all the advantages of the invention to be employed in order for the concept of the invention to be utilized. For example, it would be desirable to utilize the invention in the electrodes of the prior art by replacing the gels and liquids in some embodiments of the prior art by the adhesive/ionic substance element of the invention. In such embodiments even though the receptacles and electrode attachment gear of the prior art may not be eliminated, the properties of the element would nonetheless facilitate the elimination of most of the messiness and difficulties of handling of the ionic substance that have been associated with the prior art. The invention contemplates any use of the adhesive/ionic substance element in an iontophoretic electrode, the only requirement being that the element is disposed in the electrode in such a manner that upon application of the electrode to a body and upon application of a electric current to the electrode the ionic substance will be driven into the body.

The invention may be practiced by applying an electrode containing a mixture of the ionic substance and an adhesive material to the body and then driving an electric current through the mixture and into the body thereby introducing the ionic substance into the body. Further, the invention may be practiced by employing the electrode according to the invention with a combination iontophoretic/electrical pulse stimulator. The invention contemplates that the electrode may be used in an iontophoretic generator that also includes an electrical nerve stimulator, an electrical muscle stimulator or a combination of both types of stimulation.

The invention contemplates one stage in a method of diagnosis of cystic fibrosis in which a mixture of pilocarpine nitrate in an adhesive material is applied to the body, an electric current is driven through the mixture and into the body to drive the pilocarpine nitrate into the body, the body is allowed to produce sweat, and the sweat is analyzed to determine whether cystic fibrosis is present. Such a method of diagnosis facilitates the mass application of such a diagnostic process, for example in the mass screening of newborn infants for cystic fibrosis. Numerous other features, objects and advantages of the invention will become apparent from the following detailed description when read in conjunction with the accompanying drawing.

DESCRIPTION OF THE PREFERRED EMBODIMENT

Figure 1:
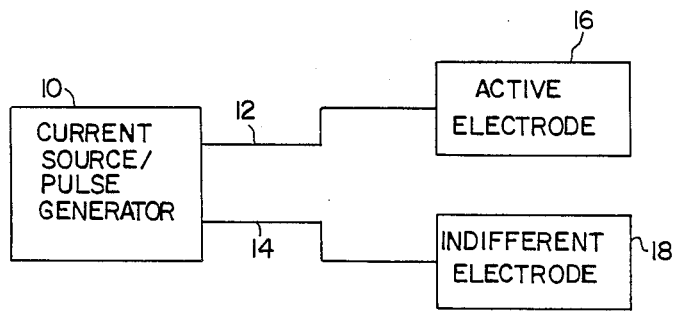
FIG. 1 is a diagrammatic illustration showing an exemplary iontophoretic system employing electrodes according to the invention.

As previously pointed out, the invention particularly lends itself to iontophoretic electrodes of varying types, shapes and configurations. For exemplary purposes herein, an iontophoretic system is illustrated in diagrammatic form in FIG. 1. The system includes current source 10 which is electrically coupled through leads 12 and 14 to electrodes 16 and 18 respectively. For purposes of illustration, electrode 16 is labeled the "active" electrode while electrode 18 is labeled the "indifferent" electrode, although the positions may be reversed. It is also possible that in some embodiments of electrodes according to the invention that an electrode that is active when the current is flowing in one direction in the system will become an indifferent electrode when the current is flowing the opposite direction in the system. Leads 12 and 14 may be wires or they may be any other means for electrically coupling the current source 10 and the electrodes 16 and 18.

Figure 2:
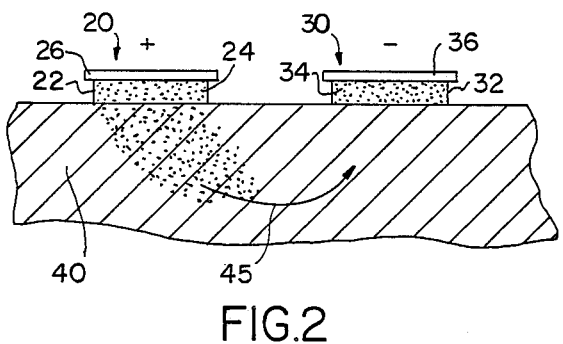
FIG. 2 is a sectional diagrammatic view of a pair of electrodes applied to the body, illustrating the iontophoretic process.

FIG. 2 shows a sectional view of a pair of electrodes 20 and 30, according to one embodiment of the invention, placed upon body 40 to illustrate the iontophoretic process. Each electrode (20 and 30) comprises an element (22 and 32) composed of an adhesive material mixed with an ionic substance (24 and 34) and a backing sheet (26 and 36). The positively charged ionic substance 24 in element 22 of electrode 20 is the drug or other chemical which is to be introduced into the body. Electrodes 20 and 30 may be coupled to a current source, such as 10, through leads, such as 12 and 14 (not shown in FIG. 2). The current source 10 may also include a source of electrical pulses, which may be of a type suitable for either nerve or muscle stimulation. The leads 12 and 14 may be attached to electrodes 20 and 30 in any conventional manner. When a current is generated by a current source, such as 10, and applied to electrodes 20 and 30 in place upon body 40, a current will flow through body 40 in the direction shown at arrow 45. The current will cause positively charged ionic substance 24 to be driven out of electrode 20 into body 40. It should be understood that the word body is used in its most general sense, and can include plant, animal and human bodies.

Figure 3:
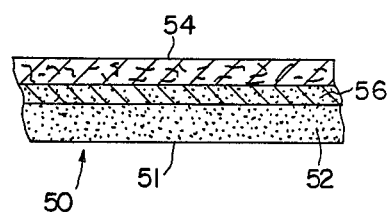
FIG. 3 is a sectional view of an electrode according to a preferred embodiment of the invention.

FIG. 3 shows a sectional view of an alternative preferred embodiment of the electrode according to the invention. In this embodiment a sheet 51 of the inventive adhesive and ionic substance mixture is affixed to a backing sheet 54 by means of adhesive 56. The backing sheet 54 may be made of cloth, paper, polymer, fiber or any other similar material. In some embodiments it may be desirable to use a conductive material as a backing sheet, as for example when the backing sheet is attached to a lead such as 12 and serves as a current disperser. In other embodiments a current dispersing element (not shown) may be inserted between backing sheet 54 and sheet 51. Adhesive 56 may be either the adhesive used in making sheet 51 or any other suitable adhesive. A lead such as 12 may be affixed to electrode 50 in any conventional manner.

Figure 4:
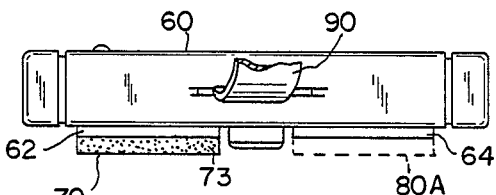
FIG. 4 is a side view of an iontophoretic current generator employing an alternative preferred embodiment of an electrode according to the invention, with one electrode in place.
Figure 5A:
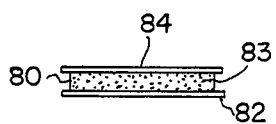
FIG. 5a is a side view showing the electrode that is employed with the current generator of FIG. 4, in the form in which the electrode may be manufactured and sold.
Figure 5B:
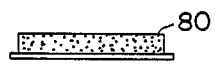
FIG. 5b is a side view of the electrode of FIG. 5a showing one of the protective covering sheets removed, in preparation for the application of the electrode to the current generator of FIG. 4.

An ambulatory iontophoretic system employing another preferred embodiment of the invention is shown in FIG. 4. In this system the current source pulse generator is contained within housing 60 to which electrode plates 62 and 64 are directly affixed. The electrodes are applied to plates 62 and 64. In FIG. 4 an electrode, 70, is shown applied to plate 62. The position of the second electrode would take if it were applied to plate 64 is shown in ghost at 80a. An electrode such as may be applied to plate 64 of the iontophoretic current generator of FIG. 4 is shown in FIG. 5a as it may be manufactured and sold. The electrode element 80, composed of a sheet of the inventive composition, has its broad surfaces covered by protective release liners 82 and 84. The release liners 82 and 84 are preferably of polyethylene coated or wax impregnated paper, but may also be formed of plastic, cloth, fiber, or any other suitable material possessing release characteristics. FIG. 5b shows the electrode of FIG. 5a with the upper protective liner 84 removed in preparation for applying electrode element 80 to a plate such as 64 of the iontophoretic current generator of FIG. 4. It may be appreciated that the invention makes compact, ambulatory iontophoretic current generators such as shown in FIG. 4 much more practical because of the simplicity of the electrodes.

Figure 6:
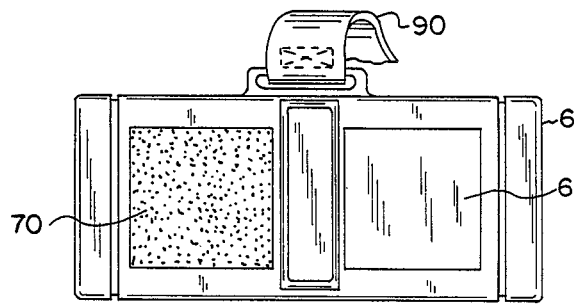
FIG. 6 is a bottom view of the iontophoretic current generator of FIG. 4.

FIG. 6 shows the bottom view of the iontophoretic current generator of FIG. 4 having one electrode 70 attached. This view shows the square shape of the electrode in this embodiment. Obviously, many other shapes and sizes of electrodes could be used. It will be appreciated that the electrodes of FIG. 5a could be manufactured in preformed shapes or very large sheets, in which case individual electrodes of a shape and size suitable for application to a current generator could be cut out of the large sheet as necessary. Or alternatively, the large sheet could be manufactured with partial precuts or grooves along the sheet defining the boundaries of individual electrodes, so that the individual electrodes could be detached from the sheet along the cuts or grooves.

One of the features of the invention is the fact that in the embodiment shown in FIGS. 4 and 6, electrodes 70 and 80 serve not only as a means of holding the electrodes to the body, but also as a means for holding the iontophoretic system to the body. In the embodiment shown, safety strap 90 is provided as an auxiliary means for holding the system to the body due to the substantial mass of the current generator.

Another important feature of the invention is the aforesaid function of the electrode elements such as 22, 51 and 70 being the means for holding the ionic substance in such a manner that it is available for being driven into the body by the current. If, for example, a non-adhesive conducting layer that is permeable to the ionic substance is positioned between the elements 22, 51 or 70 and the body, this element would still perform the inventive and very useful function of holding the ionic substance in a non-messy and precisely controllable manner, although it may no longer fulfill the additional function of attaching the electrode, or the electrode and iontophoretic generator to the body. Similarly, if the invention is fully understood, it will be appreciated that many other embodiments of the invention may be devised.

In the embodiments shown, electrode elements 22, 51 and 70 are the active electrodes and the ionic substance 24, 52 and 73 respectively is positively charged and comprises the substance which it is desired to introduce into the body. In this embodiment electrodes 32 and 80, are the indifferent electrodes and the ionic substance 34 and 83 may have either positive or negative charge, or both. In some embodiments it may be desirable to drive a negatively charged ionic substance into the body, in which case the negative electrode would be active and the embodiments, for example embodiments in which the electrode elements such as 30 and 80 are applied to an iontophoretic generator in which the polarity of the electrode plates such as 62 and 64 is reversible or embodiments in which simultaneous delivery of both positive and negative drugs is desirable, the ionic substance 34 and 83 may also be a substance which it is desired to introduce into the body. In some instances it may be desired to introduce more than one substance of the same charge into the body and thus several ionic substances may be included in the same active electrode element.

The composition of the electrode elements such as 22, 32, 51, 70 and 80 of the invention may include ingredients to control or alter the physical properties of the element. Tackifiers may be added to control the tackiness, humectants and water may be added to control the wetness, preservatives may be added to extend the shelf life and/or the useful life of the product inert fillers may be added to control the bulk or dilute or adjust other properties. Preferably the physical properties are adjusted so that the elements 22, 32, 51, 70 and 80 are solid, that is, their consistency is such that the material does not perceptively flow. It is also contemplated that the composition may be manufactured and sold in a liquid form which upon application to the plates such as 62 or backing materials such as 26, 36 and 54 changes to a tacky liquid or solid form by drying, chemical reaction or otherwise.

Ingredients may also be added to the composition to color it. The coloring of the electrode element may be used as a code to identify the ionic substance which is admixed in the particular electrode or electrode element.

The iontophoretic electrode composition of this invention consists essentially of an adhesive material in admixture with ionic substance. The preferred adhesive contains one or more synthetic or naturally occurring polar, non-ionic polymers, a tackifier, a humectant and water.

As stated above, the adhesive materials of this invention contain essentially non-ionic, polar, synthetic and/or naturally occurring polymeric compounds. The non-ionic nature is preferable so that the adhesive does not interfere with the iontophoretic process. The polar nature is preferable since it ensures that the ionic drug will be soluble in the adhesive material. Essentially non-ionic, polar synthetic polymers suitable for use in the adhesive material of the iontophoretic electrodes of this invention are exemplified by the following materials: poly(acrylamide), poly(2-hydroxyethyl acrylate), poly(2-hydroxypropyl acrylate), poly(n-vinyl-2-pyrollidone), poly(n-methylol acrylamide), poly(diacetone acrylamide), poly (2-hydroxyethyl methacrylate), poly (2-hydroxy propyl methacrylate), poly(vinyl alcohol), poly (ethylene oxide), poly (propylene oxide), and poly (allyl alcohol). Hydroxyl functional condensation polymers (i.e. polyesters polycarbonates, polyurethanes) are also examples of esstially non-ionic, polar synthetic polymers suitable for use in the adhesive material of the iontophoretic electrodes of the invention. Essentially non-ionic, polar naturally occurring polymers (or derivatives thereof) suitable for use in the adhesive material of the iontophoretic electrodes of this invention are exemplified by the following materials: cellulose ethers, methyl cellulose ethers, cellulose and hydroxylated cellulose, methyl cellulose and hydroxylated methyl cellulose, gums such as guar, locust, karaya, xanthan and gelatin.

Tackifiers which may be included in the adhesive composition of this invention are exemplified by the following materials: polybutene, terpene resins, rosin resins, parafinic oils, glycols, glycerine, and sorbitol. Humectants which may be included are exemplified by: glycols, glycerine and sorbitol A variety of ionic substances intended to be introduced into the body may be intermixed with the adhesive to form the inventive composition. Some of the ionic substances are pilocarpine nitrate, lidocaine hydrochloride, hydrocortisone derivatives, acetic acid, fluoride, penicillin and dexamethasone sodium phosphate.

The electrodes formed using these ionic substances are generally used as the active electrodes, although it would be possible to use them also for the indifferent electrodes in certain circumstances.

Other ionic substances which may be mixed with the adhesive to form the inventive composition are salts such as potassium sulfate or sodium chloride The electrodes formed using these ionic substances generally would be useful only for the indifferent electrodes.

The following examples are illustrative of the processes and materials used to obtain the electrode compositions of the invention.

EXAMPLE I 11.3 grams of pilocarpine nitrate were dissolved in 270 ml of deionized water in a 1 liter flask. To the former solution 300 grams of glycerine followed by 300 grams of polybutene were added. Next, a previously mixed combination of 225 grams of gelatin and 37.5 grams of polyvinyl pyrrolidone was added. The resulting layers of components were stirred until the mixture thickened and was difficult to stir (about 2–3 minutes). A water bath heated the mix for about one hour at which time the temperature was approximately 65° C., and the mix was again fluid. The fluid mix, with continued heating, was stirred five minutes or longer to insure homogeneity, at which point the temperature was approximately 75° C. The composite was poured into a polyethylene plastic pan, covered with aluminum foil and refrigerated until set.

About 3 hours later the composite was weighed into approximately 100 gram amounts. These were placed within a 6½"×6½"×⅛" brass frame between sheets of Mylar. The sandwiched composite was placed between the platens of a compression molder at about 55° C. and subjected to 20,000 lb. ram force for 2 to 3 minutes.

The sheet of pressed composite was cut with a stainless steel scalpel into squares 1⅛"×1⅛" while still between Mylar. The electrodes formed in this manner were applied to an electrode plate 62 of an iontophoretic generator such as shown in FIGS. 4 and 6, as previously described, with relative ease. After the iontophoretic process described above was completed it was found that there was good uniform pilocarpine introduction into the body under the entire pad with minimal hot spots and burning.

EXAMPLE II

The materials and procedures as in Example I were used except that 11.3 grams potassium sulfate was substituted for the pilocarpine nitrate, and 10 ml of 4% FD4C Blue 1 was substituted for 10 ml of the deionized water. The electrode thus formed was found to be easily applied to the electrode plate 64 of the iontophoretic current generator shown in FIGS. 4 and 6 and used with good results as the indifferent electrode during the above-described iontophoretic process.

EXAMPLE III

The same materials and procedures as in Example I were used, except that the pilocarpine nitrate was omitted. After the composite had solidified, 98 g of the composite was cut, remelted and mixed with 10 ml of 20% lidocaine solution (2% drug by weight). After resolidification this was made into pads and used in the iontophoretic process with good results as in Example I.

The various components, including the adhesive and ionic substance given in the examples, and any other components which may be used, are preferably provided in such relative amounts as to form a flexible, self-supporting material with substantial shape retention, which is adhesive and which is electrically conductive. The components may be adjusted to form a composition of other physical consistency, as discussed above, if desired.

In terms of the percentage of weight of the total adhesive composition it has been found that the following weight percentages f the following components given in the examples provides electrodes of desirable adhesiveness and physical consistency:

| Component | Percent of Weight |
| --- | --- |
| polyvinyl pyrrolidone | 2% to 7% |
| gelatin | 15% to 35% |
| glycerin | 20% to 35% |
| polybutene | 15% to 30% |
| water | 20% to 35% |

Further, it has been found that polybutene having a molecular weight between 1000 and 3000 is preferable.

The composition with pilocarpine nitrate may be used in a method for diagnosis of cystic fibrosis. In this method the mixture of pilocarpine nitrate and an adhesive material is applied to the body, and electrical current is driven through the mixture to drive the pilocarpine nitrate into the body. The body is then allowed to sweat and the sweat is analyzed for its chloride or sodium content to determine the presence of cystic fibrosis, as disclosed in the prior art. The invention permits precise control of the pilocarpine nitrate introduced into the body. At the same time it substantially simplifies the medical procedures necessary to introduce the pilocarpine nitrate, thus making it much more practical to use the diagnostic method as a means of screening large numbers of persons, such as all newborn infants, for cystic fibrosis. The more controlled and easier application also results in the iontophoretic method being much more practical with the other ionic substances listed above. It will be appreciated that the same advantage, and other advantages may be obtained with any ionic substances for which the iontophoretic process has been shown, or will be shown to be applicable.

While the invention has been described above in connection with the particular embodiments and examples, one skilled in the art will appreciate that the invention is not necessarily so limited and that numerous other embodiments, examples, uses and modifications of and departures from the embodiments, examples and uses may be made without departing from the inventive concepts.

What is claimed is:

1. A device for use in iontophoretically introducing an ionic substance into body tissue through the skin of a patient, comprising:
   an insulative casing;
   a source of direct electrical current, mounted within said casing;
   active electrode plate means mounted on the exterior of said casing for removably mounting on said casing an active electrode element containing said ionic substance and for electrically coupling said active electrode element to said current source;
   indifferent electrode plate means mounted on the exterior of said casing for removably mounting on said casing an indifferent electrode element and for electrically coupling said indifferent electrode element to said current source;
   an adhesive active electrode element containing said ionic substance, removably mounted on said active electrode plate means; and
   an adhesive indifferent electrode element removably mounted on said indifferent electrode plate means;
   wherein said active and indifferent electrode elements are sufficiently adhesive to retain said housing on said skin of said patient.

2. A device as described in claim 1 wherein said active and indifferent electrode elements comprise sheets of adhesive materials.

3. A device as described in claim 1 wherein said active and indifferent electrode elements have first adhesive surfaces removably attaching said active and indifferent electrode elements to said active and indifferent electrode plate means, respectively, and have second adhesive surfaces opposed to said first adhesive surfaces whereby said active and indifferent electrode elements serve to attach said housing to said skin of said patient.

4. A device for use in iontophoretically introducing an ionic substance into body tissue through the skin of a patient, comprising:
   a casing;
   a source of direct electrical current mounted within said casing;
   first electrode mounting means mounted on the exterior of said casing for mounting on said casing a first adhesive electrode element containing an ionic substance and for electrically coupling said first adhesive electrode element to said current source;
   second electrode mounting means mounted on the exterior of said casing for mounting on said casing a second adhesive electrode element for coupling said second adhesive electrode element to said current source;
   a first adhesive electrode element containing said ionic substance, mounted on said first electrode plate means; and
   a second adhesive electrode element mounted on said second electrode plate means;
   wherein said first and second electrode elements are sufficiently adhesive to retain said housing on said skin of said patient.

5. A device according to claim 4 wherein said first and second adhesive electrode elements are sheets of adhesive.

6. A device according to claim 4 wherein said first and second adhesive electrode elements are sheets fabricated of a polar, non-ionic adhesive.

7. A method of iontophoretically introducing an ionic substance into a body, through the skin of the patient, comprising:
   selecting a source of direct electrical current of the type comprising an insulative housing and first and second electrode mounting means, said first and second electrode mounting means coupled to said source of direct electrical current;

applying a first sheet of adhesive material containing said ionic substance to said first electrode mounting means;

applying a second sheet of adhesive, conductive material to said second electrode mounting means;

mounting said source of direct electrical current to said skin of said patient by applying said first and second sheets of adhesive material to said skin of said patient; and activating said source of direct electrical current to drive said ionic substance through said skin of said patient and into said body.

8. A method according to claim 7 wherein said first sheet of adhesive material has opposing first and second adhesive surfaces, and wherein said step of applying said first sheet of adhesive material to said first electrode mounting means comprises adhering said first adhesive surface to said first electrode mounting means;

wherein said second sheet of adhesive material has opposing first and second adhesive surfaces wherein said step of applying said second sheet of adhesive material comprises adhering said first adhesive surface of said second sheet of adhesive material to said second electrode mounting means; and wherein said step of mounting said source of direct electrical current to said skin of said patient comprises adhering said second adhesive surfaces of said first and second sheets of adhesive material to said skin of said patient.

* * * * *